(12) United States Patent
Simanzhenkov et al.

(10) Patent No.: US 10,668,441 B2
(45) Date of Patent: Jun. 2, 2020

(54) HEAT DISSIPATING DILUENT IN FIXED BED REACTORS

(71) Applicant: NOVA Chemicals (International) S.A., Fribourg (CH)

(72) Inventors: Vasily Simanzhenkov, Calgary (CA); Kamal Elias Serhal, Calgary (CA); Shahin Goodarznia, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 15/762,729

(22) PCT Filed: Sep. 8, 2016

(86) PCT No.: PCT/IB2016/055365
§ 371 (c)(1),
(2) Date: Mar. 23, 2018

(87) PCT Pub. No.: WO2017/046680
PCT Pub. Date: Mar. 23, 2017

(65) Prior Publication Data
US 2018/0272303 A1    Sep. 27, 2018

(30) Foreign Application Priority Data

Sep. 14, 2015   (CA) ...................................... 2904477

(51) Int. Cl.
*B01J 8/02*   (2006.01)
*B01J 8/04*   (2006.01)
(Continued)

(52) U.S. Cl.
CPC .............. *B01J 8/025* (2013.01); *B01J 8/0453* (2013.01); *B01J 27/0576* (2013.01); *C07C 2/84* (2013.01); *C07C 5/48* (2013.01); *B01J 2208/00061* (2013.01); *B01J 2208/00513* (2013.01); *C07C 2527/057* (2013.01)

(58) Field of Classification Search
CPC .............. B01J 2208/00513; B01J 8/025; B01J 8/0453; B01J 27/0576; B01J 2208/00061; B01J 8/0257; C07C 5/48; C07C 2/84; C07C 2527/057
See application file for complete search history.

(56) References Cited

U.S. PATENT DOCUMENTS 2,267,767 A   12/1941   Thomas
2,478,194 A   8/1949    Houndry
(Continued)

OTHER PUBLICATIONS

Peri, J.B. and Hensley, A.L., Jr.; The Surface Structure of Silica Gel; The Journal of Physicdal Chemistry; vol. 72, No. 8, Aug. 1968, pp. 2926-2933.

(Continued)

*Primary Examiner* — Ali Z Fadhel
(74) *Attorney, Agent, or Firm* — Gary F. Matz

(57) ABSTRACT

Incorporating into a fixed bed reactor for an exothermal reaction having a catalyst supported on a support having a thermal conductivity typically less than 30 W/mk within the reaction temperature control limits heat dissipative particles having a thermal conductivity of at least 50 W/mk less than 30 W/mk within the reaction temperature control limits helps control the temperature of the reactor bed.

3 Claims, 1 Drawing Sheet

(51) Int. Cl.
*B01J 27/057* (2006.01)
*C07C 2/84* (2006.01)
*C07C 5/48* (2006.01)

(56) References Cited

U.S. PATENT DOCUMENTS

| | | | |
|---|---|---|---|
| 3,420,911 A | 1/1969 | Woskow et al. | |
| 3,420,912 A | 1/1969 | Woskow et al. | |
| 6,013,741 A | 1/2000 | Ohtani et al. | |
| 6,069,271 A * | 5/2000 | Tanimoto | B01J 8/067 422/198 |
| 8,435,920 B2 | 5/2013 | White et al. | |
| 2002/0183198 A1* | 12/2002 | Gaffney | B01J 23/002 502/215 |
| 2002/0183199 A1* | 12/2002 | Bogan, Jr. | B01J 23/002 502/215 |
| 2002/0188149 A1* | 12/2002 | Bogan, Jr. | B01J 23/002 558/321 |
| 2003/0006026 A1* | 1/2003 | Matsumoto | B01J 8/001 165/157 |
| 2012/0016171 A1* | 1/2012 | Kustov | B01J 23/002 585/662 |
| 2014/0134067 A1* | 5/2014 | Hartvigsen | F28F 7/00 422/206 |

OTHER PUBLICATIONS

Watanabe, Hiromu and Koyasu, Yukio; New synthesis route for Mo—V—Nb—Te mixed oxides catalyst for propane amoxidation; Applied Catalysis A: General 194-195 (2000), pp. 479-485.

* cited by examiner

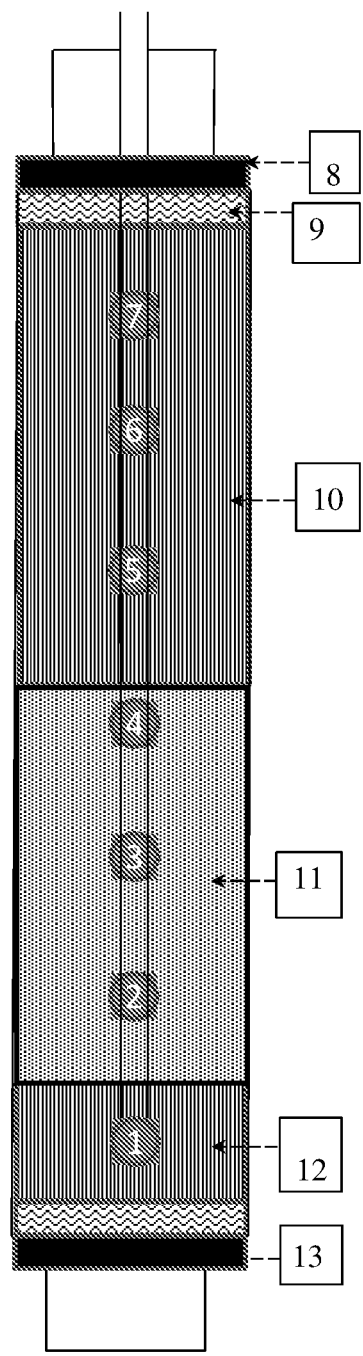

HEAT DISSIPATING DILUENT IN FIXED BED REACTORS

TECHNICAL FIELD

The present invention relates to the use of a heat dissipating diluent in fixed reactors to seek to reduce the risk of a runaway reaction. Many chemical reactions are exothermic, and particularly treatments of hydrocarbons in fixed beds. A problem can arise if the rector starts to become too hot. As the reactor heats the rate of reaction increases adding more heat to the reactor further increasing the rate of reaction. In many instances for safety reasons it is necessary to have "kill systems" designed into the reactor to rapidly shut down a reactor.

BACKGROUND ART

U.S. Pat. No. 6,013,741 issued Jan. 11, 2000 to Ohtani et al., assigned to Mitsui teaches the design of a reactor to permit the rapid introduction of a kill gas into a fluidized bed reactor to rapidly stop a reaction in the event of an equipment failure.

U.S. Pat. No. 8,435,920 issued May 7, 2013 to White et al., assigned to Eltron Research & Development, Inc. refers at Col. 1 lines 45 through 66 to Lyon which teaches the use of metal oxide catalysts in the partial oxidation of hydrocarbon feeds. The reference does not refer to using inert metallic dilluents in a reactor bed.

There are a number of United States patents assigned to Petro-Tex Chemical Corporation issued in the late 1960's that disclose the use of various ferrites in a steam cracker to produce olefins from paraffins. The patents include U.S. Pat. Nos. 3,420,911 and 3,420,912 in the names of Woskow et al. The patents teach introducing ferrites such as zinc, cadmium, and manganese ferrites (i.e. mixed oxides with iron oxide). The ferrites are not inert and release oxygen to react with the hydrocarbon stream. The ferrites are introduced into a dehydrogenation zone at a temperature from about 250° C. up to about 750° C. at pressures less than 100 psi (689.476 kPa) for a time less than 2 seconds, typically from 0.005 to 0.9 seconds. The reaction appears to take place in the presence of steam that may tend to shift the equilibrium in the "wrong" direction. Additionally the reaction does not take place in the presence of a catalyst.

U.S. Pat. No. 2,267,767, issued Dec. 30, 1941 to Thomas, assigned to Universal Oil teaches the use of non porous metallic substrates as supports for catalysts for the treatment of hydrocarbons. The metallic substrates are treated with non aqueous solutions of a metallic alkoxide and an alkyl ortho silicate. The substrate appears to be a component for the reaction. The metal oxides may be alumina, zirconia, thoria, vanadia, magnesia and other metal oxides which are active in the cracking and or reforming reactions.

U.S. Pat. No. 2,478,194 issued Aug. 9, 1949 assigned to Houdry Process Corporation teaches a composite shaped catalyst and support comprising a metallic component such as iron or steel. The metallic component may take a number of shapes such as an "I" a cross, or even the shape of a child's jack. The catalytic component is then applied to the metallic support to form the catalyst. The metallic component provides an oxidation promoter not an inert heat sink.

The fixed bed reactor is a workhorse of the petrochemical and refining industry. In commercial reactors the ratio of reactor diameter to effective particle diameter is at least 50:1 generally greater than 500:1. Catalyst supports generally have a low thermal conductivity. Under these conditions there is a low transfer of heat from the interior of the fixed bed to the reactor wall where heat may be dissipated. These conditions may lead to localized hot spots which can be the center for a runaway reaction, particularly for exothermic reactions.

The present invention seeks to provide a fixed bed of catalyst and a metallic diluent having a thermal conductivity of greater than 30 W/mK (watts/meter Kelvin) within the reaction temperature control limits to permit the transfer of heat within the bed and also out of the bed.

DISCLOSURE OF INVENTION

In one embodiment the present invention provides a process for conducting an exothermic reaction in the presence of a fixed bed comprising supported catalyst the improvement comprising incorporating into the bed from 5 to 90 wt. % based on the entire weight of the catalyst bed of one or more inert non catalytic heat dissipative particles having a melting point at least 30° C. above the temperature upper control limit for the reaction, a particle size within 1 mm to 15 mm and a thermal conductivity of greater than 50 W/mK (watts/meter Kelvin) within the reaction temperature control limits.

In a further embodiment the particulates are metals, alloys and compounds having a thermal conductivity of greater than 150 W/mK (watts/meter Kelvin) within the reaction temperature control limits.

In a further embodiment the inert heat dissipative particles comprise silver, copper, gold, steel, stainless steel, molybdenum and tungsten.

In a further embodiment the reaction involves one or more of cracking, isomerization, oxidative coupling, oxidative dehydrogenation, hydrogen transfer, polymerization, and desulphurization of a hydrocarbon or any other exothermic reaction.

In a further embodiment the particulates are metallic.

In a further embodiment the particulates have a size from 0.5 mm to 75 mm.

In a further embodiment the process is the oxidative coupling of one or more $C_{1-4}$ hydrocarbons.

In a further embodiment the process is the oxidative dehydrogenation of one or more $C_{2-4}$ hydrocarbons.

In a further embodiment the process is conducted using a mixed feed of ethane and oxygen in a volume ratio from 70:30 to 95:5 at a temperature upper control limit less than 420° C. at a gas hourly space velocity of not less than 280 $hr^{-1}$ and a pressure from 80 to 1000 kPa (about 0.8 to 10 atmospheres).

In a further embodiment the process has a conversion of ethane of not less than 90%.

In a further embodiment t the gas hourly space velocity of the process is not less than 280 $hr^{-1}$ (preferably at least 1000 $hr^{-1}$).

In a further embodiment the temperature upper control limit is less than 400° C.

In a further embodiment the catalyst has the empirical formula $Mo_gV_hTe_iNb_jPd_kO_l$, wherein g, h, i, j, k and l are the relative atomic amounts of the elements Mo, V, Te, Nb, Pd and O, respectively, and when g=1, h ranges from 0.01 to 1.0, i ranges from 0.01 to 1.0, j ranges from 0.01 to 1, $0.001<k\leq0.10$ and l is dependent on the oxidation state of the other elements.

In a further embodiment the catalyst has the empirical formula $$V_xMo_yNb_zTe_mMe_nO_p$$

wherein Me is a metal selected from the group consisting of Ta, Ti, W, Hf, Zr, Sb and mixtures thereof; and x is from 0.1 to 3 provided that when Me is absent x is greater than 0.5;

y is from 0.5 to 1.5;

z is from 0.001 to 3;

m is from 0.001 to 5;

n is from 0 to 2;

and p is a number to satisfy the valence state of the mixed oxide catalyst.

In a further embodiment the crystalline phase of the catalyst has the formula $Mo_{1.0}V_{0.22-0.35}Te_{0.10-0.20}Nb_{0.15-0.19}O_d$, preferably $Mo_{1.0}V_{0.22-0.33}Te_{0.10-0.16}Nb_{0.15-0.18}O_d$ where d is a number to satisfy the valence of the oxide (as determined by PIXE)

In a further embodiment the crystalline phase of the catalyst the amount of the phase having the formula $(TeO)_{0.39}(Mo_{3.52}V_{1.06}Nb_{0.42})O_{14}$ is above 75 wt. % as determined by XRD In a further embodiment the crystalline phase of the catalyst the amount of the phase having the formula $(TeO)_{0.39}(Mo_{3.52}V_{1.06}Nb_{0.42})O_{14}$ is above 85 wt. % as determined by XRD.

BRIEF DESCRIPTION OF DRAWINGS

FIG. 1 is a schematic diagram of the fixed bed reactor used to conduct the experiments.

BEST MODE FOR CARRYING OUT THE INVENTION

Numbers Ranges

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present invention desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

The Catalyst

The present invention is suitable for use with any fixed bed reactor in which there is a desire to have a better control over the heat flow within the fixed bed and also the transfer of heat into or out of the bed. Since the inert non catalytic heat dissipative particles present in the bed have a thermal conductivity of greater than 50, in some embodiments 100, in further embodiments 150, still further embodiments 200, W/mK (watts/meter Kelvin) within the reaction temperature control limits, the inert non catalytic heat dissipative particles may transfer heat directly to the walls of the reactor improving the cooling homogeneity (or heating if the wall are heated) and reduction of hot spots in the fixed bed.

The reactions may comprise one or more of oxidative cracking, isomerization, oxidative coupling, oxidative dehydrogenation, hydrogen transfer, polymerization, and desulphurization of a hydrocarbon or any other exothermic reaction. In some embodiments the reaction is oxidative dehydrogenation of a $C_{2-4}$ alkane or the oxidative coupling of a $C_{1-4}$ alkane. These last two reactions are of concern as the feed comprises a hydrocarbon and oxygen. If the ratio of oxygen to hydrocarbon exceeds the lower flammability (explosive) limit and the reaction temperature of the bed exceeds the ignition temperature of the mixture there is a certainty of an undesired outcome.

In some methods of carrying out such reactions the reactant stream is diluted with steam or an inert gas such as nitrogen to keep the reactive mixture below the lower flammability (explosive) limit. This type of approach tends to reduce the per pass conversion of the reactants and product stream needs to be separated, typically using some type of unit like a $C_2$ splitter which is energy intensive and greenhouse gas producing.

Another approach is to operate such reactions above the lower flammability (explosive) limit but at a temperature below the auto-ignition temperature of the feed. In such a method of operation it is critical to have a uniform temperature within the bed (i.e. no hot spots) and to have a good control over the removal of heat from the fixed bed.

There are a number of catalyst which may be used for oxidative dehydrogenation.

In some embodiments the catalyst may have the composition $Mo_aV_bNb_cSb_dX_e$. X is nothing or Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, Mn and/or W; a is 0.5-0.9, b is 0.1-0.4, c is 0.001-0.2, d is 0.001-0.1, e is 0.001-0.1 when X is an element.

In some embodiments the catalyst has the formula:

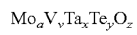

wherein, a is 1.0, v is about 0.01 to about 1.0, x is about 0.01 to about 1.0, and y is about 0.01 to about 1.0, and z is the number of oxygen atoms necessary to render the catalyst electronically neutral. The catalyst may be supported on typical supports including porous silicon dioxide, ignited silicon dioxide, kieselgur, silica gel, porous or nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride or silicon carbide, but also glass metal-oxide or metal networks. In some embodiments titanium oxide.

In some embodiments the catalyst may have the formula:

$$V_xMo_yNb_zTe_mMe_nO_p$$

wherein Me is a metal selected from the group consisting of Ta, Ti, W, Hf, Zr, Sb and mixtures thereof; and
x is from 0.1 to 3 provided that when Me is absent x is greater than 0.5;
y is from 0.5 to 1.5;
z is from 0.001 to 3;
m is from 0.001 to 5;
n is from 0 to 2;
and p is a number to satisfy the valence state of the mixed oxide catalyst.

In some examples, the catalyst may have the empirical formula (measured by PIXE):

$$Mo_{1.0}V_{0.22-0.33}Te_{0.10-0.16}Nb_{0.15-0.18}O_d$$

wherein d is a number to satisfy the valence of the oxide.

In some embodiments, the catalyst may have the empirical formula $Mo_gV_hTe_iNb_jPd_kO_l$, wherein g, h, i, j, k and l are the relative atomic amounts of the elements Mo, V, Te, Nb, Pd and O, respectively, and when g=1, h ranges from 0.01 to 1.0, i ranges from 0.01 to 1.0, j ranges from 0.01 to 1, $0.001<k\leq0.10$ and l is dependent on the oxidation state of the other elements. The addition of small amounts of Pd into the catalyst provides an increase in activity while maintaining high selectivity for ethylene.

In an embodiment of this Pd containing catalyst, the relative atomic amount of the element vanadium, indicated by subscript h, ranges from 0.1 to 0.5. In another embodiment of the catalyst, h ranges from 0.2 to 0.4. In a further embodiment of then catalyst h ranges from 0.25 to 0.35.

In an embodiment of this Pd containing catalyst, the relative atomic amount of the element tellerium, indicated by subscript i, ranges 0.05 to 0.4. In another embodiment of the catalyst, i ranges from 0.08 to 0.3. In a further embodiment of the catalyst, i ranges from 0.10 to 0.25.

In an embodiment of this Pd containing catalyst, the relative atomic amount of the element niobium, indicated by subscript j, ranges from 0.05 to 0.4. In another embodiment of the catalyst, j ranges from 0.08 to 0.3. In a further embodiment of the catalyst, j ranges from 0.10 to 0.25.

Hydrothermal synthesis for preparation of mixed metal oxide catalysts is known in the art, its advantages over conventional preparation methods such as solid-state reaction and dry-up are covered in Watanabe, et al., "New Synthesis Route For Mo—V—Nb—Te Mixed Metal Oxides For Propane Ammoxidation," Applied Catalysis A: General, 194-195, pp. 479-485 (2000).

Generally a hydrothermal synthesis step is used for preparation of the catalyst prior to addition of the Pd compound. Compounds containing elements Mo, V, Nb, and Te and a solvent are mixed to form a first admixture. The first admixture is then heated in a closed vessel for from 24 to 240 hours. One useful solvent for the hydrothermal synthesis of the first admixture is water. Any water suitable for use in chemical syntheses can be utilized, and includes, without limitation, distilled water, de-ionized, water. The amount of solvent used is not critical for the present invention.

Preparation of the admixture is not limited to addition of all compounds of Mo, V, Nb, and Te at the same time prior to heat treatment in a first closed vessel. For example, the Mo and Te compounds may be added first, followed by the V compound and eventually the Nb compound. For a further example, the process may be reversed in that the Te and Nb compounds are combined followed by addition of a mixture of the Mo and V compounds. Other sequences of addition would be apparent to a person skilled in the art. Sequence and timing of addition is not limited by these examples.

In an embodiment of the invention, the first admixture is heated at a temperature of from 100° C. to 200° C. In another embodiment of the invention, the first admixture is heated at a temperature from 130° C. to 190° C. In a further embodiment of the invention, the first admixture is heated at a temperature from 160° C. to 185° C.

Following hydrothermal synthesis of the first four components of the catalyst the first insoluble material is recovered from the first closed vessel. At this point, the first insoluble material may be dried prior to a first calcining in order to remove any residual solvent. Any method known in the art may be used for optional drying of the first insoluble material, including, but not limited to, air drying, vacuum drying, freeze drying, and oven drying.

In a further embodiment of the invention the first insoluble material may be subjected to peroxide washing prior to optional drying and prior to a first calcining. The peroxide washing treatment may take place at atmospheric pressure and room temperature (e.g. from 15° C. to 30° C.) to about 80° C., in some instances from 35° C. to 75° C. in other instances from 40° C. to 65° C. and the peroxide has a concentration from 10 to 30 wt. %, in some instances form 15 to 25 wt. %, and a time from 1 to 10 hours, in some cases from 2 to 8 hours, in other cases from 4 to 6 hours.

The first insoluble material is treated with the equivalent of from 1.3 to 3.5 mls of a 30 wt. % solution of $H_2O_2$ per gram of precursor. The treatment should be in a slurry (e.g. the precursor is at least partially suspended) to provide an even distribution of $H_2O_2$ and to control the temperature rise. For post calciniation treatment with $H_2O_2$ there is a delayed violent reaction with $H_2O_2$. The process of the present invention is an instantaneous reaction which is more controlled and safer.

Methods for calcination are well known in the art. The first calcining of the first insoluble material is conducted in a second closed vessel with an inert atmosphere. The second closed vessel for the calcination may be a quartz tube. The inert atmosphere may include any material that does not interact or react with the first insoluble material. Examples include, without limitation, nitrogen, argon, xenon, helium or mixtures thereof. The preferred embodiment of the present invention comprises an inert atmosphere comprising gaseous nitrogen.

Calcination methods for preparation of mixed metal oxide catalysts vary in the art. Variables include the time, temperature range, the speed of heating, use of multiple temperature stages, and the use of an oxidizing or inert atmosphere. For the present invention the speed of heating is not critical and may range from between 0.1° C./minute to around 10° C./minute. Also, the inert gas may be present statically or may be passed over the catalyst at flow rates where the loss of catalyst is minimized, i.e. carryover out of bed.

In an embodiment of the invention the time for the first calcining ranges from 1 hour to 24 hours. In another embodiment of the invention the time for the first calcining ranges from 3 hours to 15 hours. In the preferred embodiment of the invention the time for the first calcining ranges from 4 hours to 12 hours.

In an embodiment of the invention the first calcining takes place in an inert atmosphere at a temperature from 500° C. to 700° C. In another embodiment of the invention the first calcining takes place in an inert atmosphere at a temperature from 550° C. to 650° C. In the preferred embodiment of the invention the first calcining takes place in an inert atmosphere at a temperature of from 580° C. to 620° C. The resulting calcined product is suitable as an oxidative dehydrogenation catalyst.

In some embodiments following the first calcining, the first calcining product is mixed with a Pd component to form a second admixture. For these aspects of the invention the addition of a Pd component to the catalyst is only effective in increasing the activity of the catalyst, without significantly decreasing the selectivity, depending on the method for addition and the nature of the Pd compound used. The addition of the Pd compound must be performed following the first calcining of the first insoluble material containing the four components Mo, V, Te, and Nb. In an embodiment of the invention the Pd compound, in the form of an aqueous solution, is added dropwise to the first calcining product until saturation and the mixture forms a paste. In another embodiment of the invention, the Pd component and the first calcining product are mixed in an aqueous solution to form a slurry. In an embodiment of the invention the aqueous solution is water. Any water suitable for use in chemical syntheses can be utilized, and includes, without limitation, distilled water and de-ionized water. The amount of solvent used is not critical for the present invention.

The amount of Pd component added, either in dropwise fashion or in a slurry, will correspond roughly with 0.044 $mmol_{Pd}/g_{ODH\ catalyst}$ to yield a final relative atomic amount of Pd, represented by the subscript e in the formula $Mo_aV_bTe_cNb_dPd_eO_f$, between 0.001 and 0.1.

The nature of the Pd compound used must be free of halogens. One useful Pd component is tetra-amine Pd nitrate, chemically represented by the formula $[(NH_3)_4Pd](NO_3)_2$.

Before the second calcining the second admixture, the product may be dried using any method known in the art, including, but not limited to, air drying, vacuum drying, freeze drying, and oven drying.

The second calcining is performed under conditions and follows the same limitations as those applicable to the first calcining. The resulting second insoluble material is retrieved from the second closed vessel and can be used directly as a catalyst for ODH, using conditions where the only atmospheric components exposed to the catalyst are oxygen and ethane. The ratios of oxygen and ethane and the temperature used for the ODH process are such that the upper explosive limit is not triggered. The ability to perform ODH using this catalyst whereby there is no dilution of the reactants with nitrogen or other inert gas or water confers a commercial advantage as costly downstream processes for the removal of excess oxygen or any unwanted byproducts are not required or are limited in nature.

In some embodiments the catalyst may have the formula:

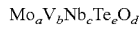

wherein:
a is from 0.75 to 1.25, preferably from 0.90 to 1.10;
b is from 0.1 to 0.5, preferably from 0.25 to 0.4;
c is from 0.1 to 0.5, preferably from 0.1 to 0.35;
e is from 0.1 to 0.35 preferably from 0.1 to 0.3; and
d is a number to satisfy the valence state of the mixed oxide catalyst.

The above MoVNbTeMeO type catalysts are heterogeneous. They have an amorphous phase and a crystalline phase. The structure and content of the crystalline phase may be influenced by treatment of the catalyst with hydrogen peroxide prior to final calcining (i.e. catalyst precursor treatment). Following such a treatment the crystalline phase of the catalyst has the formula:

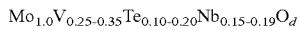

where d is a number to satisfy the valence of the oxide. In some embodiments at least 75 wt. % of the crystalline phase has the preceding formula as determined by XRD. In other embodiments at least 85 wt. % of the crystalline phase has the preceding formula as determined by XRD.

The Support

The support for the catalyst for the fixed bed may be ceramic precursor formed from oxides, dioxides, nitrides, carbides selected from the group consisting of silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron carbide, yttrium oxide, aluminum silicate, silicon nitride, silicon carbide and mixtures thereof. Typically the thermal conductivity of the support is less than 50 W/mk, preferably less than 30 W/mk within the reaction temperature control limits.

In one embodiment the support for the fixed bed may have a low surface area less than 20 m²/g, alternatively, less than 15 m²/g, alternatively, less than 3.0 m²/g for the oxidative dehydrogenation catalyst. Such support may be prepared by compression molding. At higher pressures the interstices within the ceramic precursor being compressed collapse. Depending on the pressure exerted on the support precursor the surface area of the support may be from about 20 to 10 m²/g.

The low surface area support could be of any conventional shape such as spheres, rings, saddles, etc.

It is important that the support be dried prior to use (i.e. before adding catalyst). Generally, the support may be heated at a temperature of at least 200° C. for up to 24 hours, typically at a temperature from 500° C. to 800° C. for about 2 to 20 hours, preferably 4 to 10 hours. The resulting support will be free of adsorbed water and should have a surface hydroxyl content from about 0.1 to 5 mmol/g of support, preferably from 0.5 to 3 mmol/g.

The amount of the hydroxyl groups on silica may be determined according to the method disclosed by J. B. Peri and A. L. Hensley, Jr., in *J. Phys. Chem.*, 72 (8), 2926, 1968, the entire contents of which are incorporated herein by reference.

The dried support for the fixed bed catalyst may then be compressed into the required shape by compression molding. Depending on the particle size of the support, it may be combined with an inert binder to hold the shape of the compressed part.

Loadings

Typically the catalyst loading on the support for the fixed bed catalyst provides from 1 to 30 weight % typically from 5 to 20 weight %, preferably from 8 to 15 weight % of said catalyst and from 99 to 70 weight %, typically from 80 to 95 weight %, preferably from 85 to 92 weight %, respectively, of said support. The heat dissipative particles are different from the support.

The catalyst may be added to the support in any number of ways. For example the catalyst could be deposited from an aqueous slurry onto one of the surfaces of the low surface area support by impregnation, wash-coating, brushing or spraying. The catalyst could also be co-precipitated from a slurry with the ceramic precursor (e.g. alumina) to form the low surface area supported catalyst.

The Heat Dissipative Particles for the Fixed Bed

The heat dissipative particles for the fixed bed comprises one or more non catalytic inert particulates having a melting point at least 30, in some embodiments at least 250, in further embodiments at least 500° C. above the temperature upper control limit for the reaction, a particle size in range of 0.5 to 75 mm, in some embodiments 0.5 to 15, in further embodiments in range of 0.5 to 8, desirably in the range of 0.5 to 5 mm and a thermal conductivity of greater than 30 W/mK (watts/meter Kelvin) within the reaction temperature control limits. In some embodiments the particulates are metals alloys and compounds having a thermal conductivity of greater than 50 W/mK (watts/meter Kelvin) within the reaction temperature control limits. Some suitable metals include silver, copper, gold, aluminum, steel, stainless steel, molybdenum, and tungsten.

The heat dissipative particles may have a particle size typically from about 1 to 15 mm. In some embodiments the particle size may be from about 1 mm to about 8 mm. The heat dissipative particles may be added to the fixed bed in an amount from 5 to 95 wt. %, in some embodiments 30 to 70 wt. %, in other embodiments 45 to 60 wt. % based on the entire weight of the fixed bed.

The Processes

The present invention may be used with any fixed bed exothermic reaction. In some embodiments the fixed bed reactor is a tubular reactor and in further embodiment the fixed bed reactor comprises of multiple tubes inside a shell (e.g. a shell and tube heat exchanger type construction). In a further embodiment the fixed bed reactor may comprise a number of shells in series and/or parallel. The reactions may involve one or more of cracking, isomerization, dehydrogenation including oxidative dehydrogenation, hydrogen transfer including oxidative coupling and desulphurization of a hydrocarbon.

Typically these reactions are conducted at temperatures from about 200° C. up to about 850° C. at pressures from about 80 to 21,000 kPa (about 12 to 3000 psi) in the presence of a catalyst. The hydrocarbon stream may contain a wide range of compounds including $C_{1-20}$ aliphatic, or aromatic hydrocarbons.

In some embodiments, the reactions are the oxidative coupling of aliphatic hydrocarbons, typically $C_{1-4}$ aliphatic hydrocarbons particularly methane and the oxidative dehydrogenation of $C_{2-4}$ aliphatic hydrocarbons. Such reactions may be conducted using a mixed feed of hydrocarbon, in some embodiments methane or ethane and oxygen in a volume ratio from 70:30 to 95:5 at a temperature less than 420° C. at a gas hourly space velocity of not less than 280 $hr^{-1}$, in some embodiments not less than 1000 $hr^{-1}$, in some embodiments not less than 2000 $hr^{-1}$ and a pressure from 80 to 1000 kPa (0.8 to 1.2 atmospheres). Typically, the process may have an overall conversion of from about 50 to about a 100%, typically from about 75 to 98% and a selectivity to ethylene of not less than 90%, in some instances not less than 95%, in further embodiments not less than 98%. In some cases, the temperature upper control limit is less than about 400° C., in some embodiments less than 385° C.

The resulting product stream is treated to separate ethylene from the rest of the product stream which may also contain co-products such as acetic acid, and un-reacted feed which is recycled back to the reactor.

Additionally, the product stream should have a low content of carbon dioxide, and carbon monoxide, and acetic acid, generally cumulatively in a range of less than 10, preferably less than 2 wt. %.

There are up to four competing reactions for oxidative dehydrogenation.

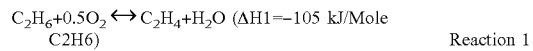

$C_2H_6 + 0.5O_2 \leftrightarrow C_2H_4 + H_2O$ ($\Delta H1 = -105$ kJ/Mole C2H6)    Reaction 1

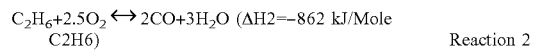

$C_2H_6 + 2.5O_2 \leftrightarrow 2CO + 3H_2O$ ($\Delta H2 = -862$ kJ/Mole C2H6)    Reaction 2

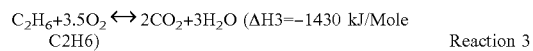

$C_2H_6 + 3.5O_2 \leftrightarrow 2CO_2 + 3H_2O$ ($\Delta H3 = -1430$ kJ/Mole C2H6)    Reaction 3

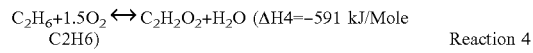

$C_2H_6 + 1.5O_2 \leftrightarrow C_2H_2O_2 + H_2O$ ($\Delta H4 = -591$ kJ/Mole C2H6)    Reaction 4

From a temperature/heat control point of view, if a catalyst preferentially leads to reaction 1, there is a lower potential for a thermal runaway.

The feed and by products may need to be separated from the product stream. Some processes may use so called dilute ethylene streams. For example, if the product stream does not contain too much ethane, for example less than about 15 vol. % the stream may be fed directly without further purification to a polymerization reactor such as a gas phase, slurry or solution reactor.

The most common separation technique would be to use a cryogenic C2 splitter. Other known ethylene/ethane separation techniques could also be used including adsorption (oil, ionic liquids and zeolite).

The present invention will now be illustrated by the following non limiting examples.

In the examples, the catalysts were prepared by a hydrothermal process as described above.

The catalyst had the empirical formula:

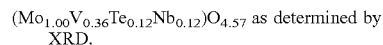

$(Mo_{1.00}V_{0.36}Te_{0.12}Nb_{0.12})O_{4.57}$ as determined by XRD.

For the comparative example, the catalyst was not treated with hydrogen peroxide. For example 1, the sample comprise a mixture of five catalyst samples treated with peroxide. The catalyst for the comparative example has a slightly higher propensity to oxidize feed to $CO_2$.

In the examples, the fixed bed reactor unit used is schematically shown in FIG. 1. The reactor was a fixed bed stainless steel tube reactor having a 2 mm (¾") outer diameter and a length of 117 cm (46 inches). The reactor is in an electrical furnace sealed with ceramic insulating material. There are 7 thermocouples in the reactor indicated at numbers 1 through 7. Thermocouples are used to monitor the temperature in that zone of the reactor. Thermocouples 3 and 4 are also used to control the heating of the reactor bed. The feed flows from the top to the bottom of the reactor. At the inlet there is a ceramic cup 8 to prevent air drafts in the reactor. Below the ceramic cup is a layer of quartz wool 9. Below the layer of quartz wool is a layer of catalytically inert quartz powder. Below the quarts powder is the fixed bed 10 comprising catalyst and diluent. Below the fixed bed is a layer of quartz powder 11, a layer of quartz wool 12 and a ceramic cup 13. At the exit of the bed was a gas analyzer to determine the composition of the product stream. The fixed bed comprised 28.83 g of catalyst and 3.85 g of diluent (32.86 g total weight % of diluent 11.7 wt. % of total bed). The GHSV was 2685 $hr^{-1}$ and the pressure was ambient.

For the examples, the bed temperature was taken as an average of the temperatures from thermocouples 2, 3 and 4. The feed stream was assumed to have the same temperature as the bed. A stoichiometric reactor block was run using the above temperature conditions using Aspen Plus simulation to calculate the overall heat release of the reactions.

Comparative Example

The heat dissipative particles in this example were quartz particles having a mean particle size of 568 micrometers. The reaction temperature (bed temperature) increased to 355° C. and then there was a thermal reaction run away.

The overall conversion to ethylene was 19% and the selectivity to ethylene was 93%. The calculated heat duty of the reactions was calculated to be a heat release of −26.28 kJ/hr. At this time there was a rapid drop in oxygen content in the product stream and a fast thermal reaction runaway began. The reaction was quenched with nitrogen.

Example 1

The heat dissipative particles were 316 Stainless Steel particles having a mean particle size of 568 micrometers. The weight % of diluent was the same as for example 1. As the steel is denser than quartz this resulted in a lower volume % of diluent in the bed. These conditions were believed to tend toward a thermal runaway. The reactor was operated to maintain an overall conversion of 19% with a selectivity to ethylene of 89%. The calculated overall heat of reaction was −31.13 kJ/hr. The temperature of the bed rose to 372° C. No runaway reaction was observed. The stainless steel diluent permitted a better release of heat through the reactor walls to control the reaction.

Example 1 shows the bed temperature did not rise above 372° C. while in the comparative example the bed temperature approached 355° followed by a thermal reaction run away. Example 1 shows dissipation in the heat of reaction.

INDUSTRIAL APPLICABILITY

The present invention helps to control/dissipate the heat generated from the oxidative dehydrogenation reaction.

The invention claimed is:

1. A process for conducting an oxidative dehydrogenation comprising:
   providing a mixed feed of ethane and oxygen in a volume ratio from 70:30 to 95:5; and
   conducting oxidative dehydrogenation of the mixed feed at a temperature less than 400° C. at a gas hourly space velocity of not less than 280 hr$^{-1}$, at a pressure from 0.8 to 102 atmospheres (80 to 1000 kPa), a conversion of ethane not less than 90%, and in the presence of a fixed bed comprising mixed metal oxide catalyst having a crystalline phase of the formula:

$$Mo_{1.0}V_{0.25-0.35}Te_{0.10-0.20}Nb_{0.15-0.19}O_d$$

where d is a number to satisfy the valence of the oxide;
wherein said mixed oxide catalyst is supported on one or more of porous silicon dioxide, ignited silicon dioxide, kieselgur, silica gel, porous or nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride or silicon carbide;
wherein said fixed bed further comprises one or more inert non catalytic heat dissipative particles comprising silver, copper, gold, steel, stainless steel, molybdenum, and tungsten in an amount from 5 to 90 wt. %, based on the weight of the fixed bed; and
wherein, said particles have a melting point at least 30° C. above a temperature upper control limit of said oxidative dehydrogenation, a particle size from 0.5 mm to 5 mm and a thermal conductivity of greater than 150 W/mK (watts/meter Kelvin) within the reaction temperature control limits.

2. A process for conducting an oxidative dehydrogenation comprising:
   providing a mixed feed of ethane and oxygen in a volume ratio from 70:30 to 95:5; and
   conducting oxidative dehydrogenation of the mixed feed at a temperature less than 400° C., at a gas hourly space velocity of not less than 280 hr$^{-1}$, at a pressure from 0.8 to 102 atmospheres (80 to 1000 kPa), a conversion of ethane not less than 90%, and in the presence of a fixed bed comprising a mixed metal oxide catalyst;
wherein the fixed bed mixed metal oxide catalyst has a crystalline phase of the formula:

$$Mo_{1.0}V_{0.25-0.35}Te_{0.10-0.20}Nb_{0.15-0.19}O_d$$

where d is a number to satisfy the valence of the oxide;
wherein in a crystalline phase of said mixed metal oxide catalyst the amount of a crystalline phase having the formula $$(TeO)_{0.39}(Mo_{3.52}V_{1.06}Nb_{0.42})O_{14}$$

is above 75 wt. % as determined by XRD;
wherein said mixed oxide catalyst is supported on one or more of porous silicon dioxide, ignited silicon dioxide, kieselgur, silica gel, porous or nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride or silicon carbide;
wherein said fixed bed further comprises one or more inert non catalytic heat dissipative particles comprising silver, copper, gold, steel, stainless steel, molybdenum, and tungsten in an amount from 5 to 90 wt. %, based on the weight of the fixed bed; and
wherein, said particles have a melting point at least 30° C. above a temperature upper control limit of said oxidative dehydrogenation, a particle size from 0.5 mm to 5 mm and a thermal conductivity of greater than 150 W/mK (watts/meter Kelvin) within the reaction temperature control limits.

3. A process for conducting an oxidative dehydrogenation comprising:
   providing a mixed feed of ethane and oxygen in a volume ratio from 70:30 to 95:5; and
   conducting oxidative dehydrogenation of the mixed feed at a temperature less than 400° C. at a gas hourly space velocity of not less than 280 hr$^{-1}$, at a pressure from 0.8 to 102 atmospheres (80 to 1000 kPa), a conversion of ethane not less than 90%, and in the presence of a fixed bed comprising a mixed metal oxide catalyst;

wherein the fixed bed mixed metal oxide catalyst has a crystalline phase of the formula:

$Mo_{1.0}V_{0.25-0.35}Te_{0.10-0.20}Nb_{0.15-0.19}O_d$ where d is a number to satisfy the valence of the oxide; wherein in the crystalline phase of the catalyst the amount of the said crystalline phase having the formula $(TeO)_{0.39}(Mo_{3.52}V_{1.06}Nb_{0.42})O_{14}$ is above 85 wt. % as determined by XRD;
wherein said mixed oxide catalyst is supported on one or more of porous silicon dioxide, ignited silicon dioxide, kieselgur, silica gel, porous or nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride or silicon carbide;
wherein said fixed bed further comprises one or more inert non catalytic heat dissipative particles comprising silver, copper, gold, steel, stainless steel, molybdenum, and tungsten in an amount from 5 to 90 wt. %, based on the weight of the fixed bed; and
wherein, said particles have a melting point at least 30° C. above a temperature upper control limit of said oxidative dehydrogenation, a particle size from 0.5 mm to 5 mm and a thermal conductivity of greater than 150 W/mK (watts/meter Kelvin) within the reaction temperature control limits.

* * * * *